US007489789B2

(12) United States Patent
Kaulberg

(10) Patent No.: US 7,489,789 B2
(45) Date of Patent: Feb. 10, 2009

(54) METHOD FOR NOISE REDUCTION IN AN AUDIO DEVICE AND HEARING AID WITH MEANS FOR REDUCING NOISE

(75) Inventor: Thomas Kaulberg, Smørum (DK)

(73) Assignee: Oticon A/S, Smorum (DK)

( * ) Notice: Subject to any disclaimer, the term of this patent is extended or adjusted under 35 U.S.C. 154(b) by 0 days.

(21) Appl. No.: 10/591,351

(22) PCT Filed: Feb. 28, 2005

(86) PCT No.: PCT/EP2005/050843

§ 371 (c)(1),
(2), (4) Date: Apr. 18, 2007

(87) PCT Pub. No.: WO2005/086536

PCT Pub. Date: Sep. 15, 2005

(65) Prior Publication Data

US 2007/0195973 A1 Aug. 23, 2007

(30) Foreign Application Priority Data

Mar. 2, 2004 (DK) ............................... 2004 00357

(51) Int. Cl.
*H04B 15/00* (2006.01)
*A61F 11/06* (2006.01)
*H04R 25/00* (2006.01)
*G10L 19/14* (2006.01)
*G10L 21/00* (2006.01)

(52) U.S. Cl. .................... 381/94.3; 381/94.1; 381/94.2; 381/94.7; 381/71.1; 381/71.14; 381/317; 704/205; 704/226

(58) Field of Classification Search ................ 381/94.3, 381/94.1, 94.7, 71.1, 71.14, 94.2, 317; 704/205, 704/226
See application file for complete search history.

(56) References Cited

U.S. PATENT DOCUMENTS

| | | | |
|---|---|---|---|
| 4,461,025 | A | 7/1984 | Franklin et al. |
| 6,523,003 | B1 | 2/2003 | Chandran et al. |
| 2004/0078200 | A1 | 4/2004 | Alves |

FOREIGN PATENT DOCUMENTS

| | | | |
|---|---|---|---|
| EP | 1 326 479 | A2 | 7/2003 |
| WO | WO-91/03042 | A1 | 3/1991 |
| WO | WO-00/05923 | A1 | 2/2000 |
| WO | WO-02/076148 | A2 | 9/2002 |

*Primary Examiner*—Vivian Chin
*Assistant Examiner*—George C Monikang
(74) *Attorney, Agent, or Firm*—Birch, Stewart, Kolasch & Birch, LLP

(57) ABSTRACT

The invention regards a method for noise reduction in an audio device whereby an electrical and/or digital signal which represents sound is routed simultaneously through:—a signal analysis path, and—a signal processing path wherein the signal amplification is individually controllable in specific frequency bands by attenuation values derived from the signal analysis path, whereby the signal in the signal analysis path is routed simultaneously through:—a first detector which identifies the presence of speech indicators in the overall signal, and—a second detector which in a predefined number of frequency bands detects the modulation amplitude, and—where attenuation values in each of the predefined frequency bands are calculated based on the combined results of the first detector and the modulation amplitude in the specific frequency band detected by the second detector,—where the attenuation values in the predefined number of frequency bands are routed to the signal processing path in order to attenuate the signal level in corresponding frequency bands.

9 Claims, 3 Drawing Sheets

METHOD FOR NOISE REDUCTION IN AN AUDIO DEVICE AND HEARING AID WITH MEANS FOR REDUCING NOISE

AREA OF THE INVENTION

The invention relates to the area of noise reduction in audio devices which are to receive an input signal either as a sound signal or as a wired or wireless signal and have means for delivering a signal to the user, which represents sound. To such devices belong usual hearing aids, cochlear or brain stem implants, headsets and noise protection devices. In the devices the received signal representing a sound signal may comprise a noise part and a speech part, whereby usually the user would like to have the noise part dampened in order to be able to better hear and understand the speech part of the signal. The invention further concerns a hearing aid with means for reducing noise.

BACKGROUND OF THE INVENTION

Numerous attempts have been made to establish a noise reduction scheme, which provides good listening comfort and good speech intelligibility at the same time.

In prior art document EP 1326479 a method of reducing noise in a signal is described whereby an input signal is supplied to an amplification unit where the input signal is subject to an auxiliary noise reduction algorithm, to generate an auxiliary signal. The auxiliary signal is used to determine a control input for the amplification unit; and the amplification unit is then controlled with the control signal, to generate an output signal with reduced noise. According to this prior art the method comprises the further steps of: detecting the presence and absence of speech utterances; and in the absence of speech, determining a noise magnitude spectral estimate; and in the presence of speech comparing the magnitude spectrum of the audio signal to the noise magnitude spectral estimate; calculating an attenuation function from the magnitude spectrum of the audio signal and the noise magnitude spectral estimate; and modifying the input signal by the attenuation function, to generate an output signal with reduced noise. This prior art technique has the problem, that it requires a speech pause in which to determine the noise magnitude spectrum. In a typical party noise situation such a pause may not be detectable and the system then has little or no clue as to how to calculate the right attenuation function.

SUMMARY OF THE INVENTION

In order to avoid the problems of the prior art, the invention suggests a method for noise reduction in an audio device whereby an electrical and/or digital signal which represents sound is routed simultaneously through:

a signal analysis path, and a signal processing path wherein the signal attenuation is individually controllable in specific frequency bands by attenuation values derived from the signal analysis path whereby the signal in the signal analysis path is routed simultaneously through:

a first detector which identifies the presence of speech indicators in the overall signal, and a second detector which in a predefined number of frequency bands detects the modulation amplitude, and where attenuation values in each of the predefined frequency bands are calculated based on the combined results of the first detector and the modulation amplitude in the specific frequency band detected by the second detector, where the attenuation values in the predefined number of frequency bands are routed to the signal processing path in order to attenuate the signal level in frequency bands.

By basing the attenuation in narrow frequency bands on the combined results of broad band speech detection and narrow band modulation amplitude it is secured that reasonable noise damping is achievable under all circumstances.

According to an embodiment of the invention the second detector calculates the modulation amplitude by tracking peeks in the signal level and tracking the noise floor in the signal level and then determines the distance between the overall level of the peeks and the noise floor. This allows the tracking parameters like attack and release times to be set according to individual preferences or these parameters may be pre-selected by the manufacturer of the device to provide overall reasonable estimates of the modulation amplitude with due regard to the auditory environment in which the device is supposed to work.

In a further embodiment the level of the noise floor in each frequency band is used to scale the calculated corresponding attenuation value, such that higher noise floor levels results in possible higher attenuation values. This scaling will aid to ensure that attenuation is only introduced when a certain noise floor level is present.

In a further embodiment the attenuation values in each specific frequency band arc calculated in the following way:

first attenuation values are calculated according to a first predefined transfer function between the modulation amplitude detected by the second detector and attenuation values whereby the first transfer function prescribes generally low attenuation values, second attenuation values are calculated according to a second predefined transfer function between the modulation amplitude detected by the second detector and attenuation values whereby the second transfer function prescribes generally high attenuation values, fading between the first and the second calculated attenuation values is performed in response to the detected speech presence indicators from the first detector.

Hereby it becomes possible to gradually shift between an aggressive noise damping used when no speech is detected and a less aggressive noise damping performed at times when speech is detected. In this way it is assured that no valuable speech cues arm lost to the user of the device.

Preferably the first detector for detecting the presence of speech indicators uses statistical information relating to possible correlation of modulation in different frequency bands. This method is known to provide a very reliable detection of the presence of speech in a signal.

For hearing aid users it is even more challenging to understand speech in noisy situations. According to the invention a hearing aid with an advanced noise processing scheme is suggested, which will improve both the listening comfort for the user and the ability to understand speech in noisy situations.

DESCRIPTION OF A PREFERRED EMBODIMENT

Figure 1:
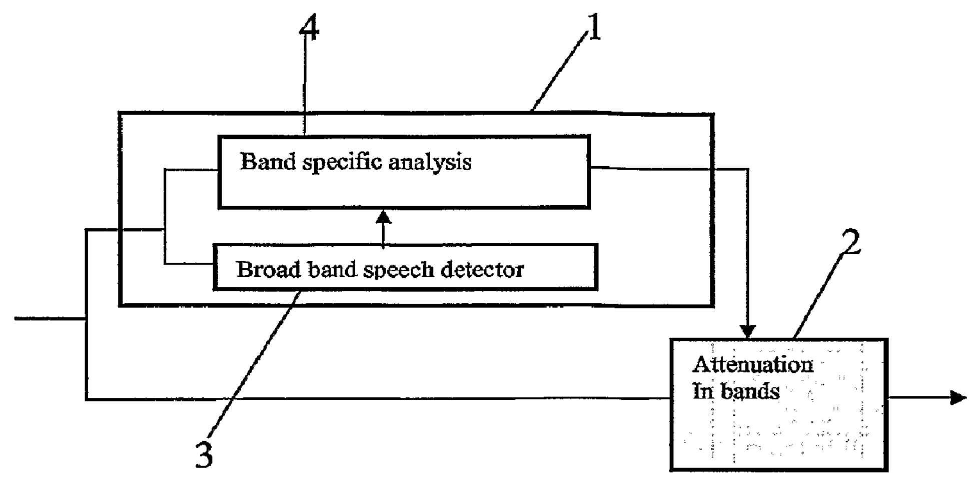
FIG. 1 is an overall block diagram displaying the method.
Figure 2:
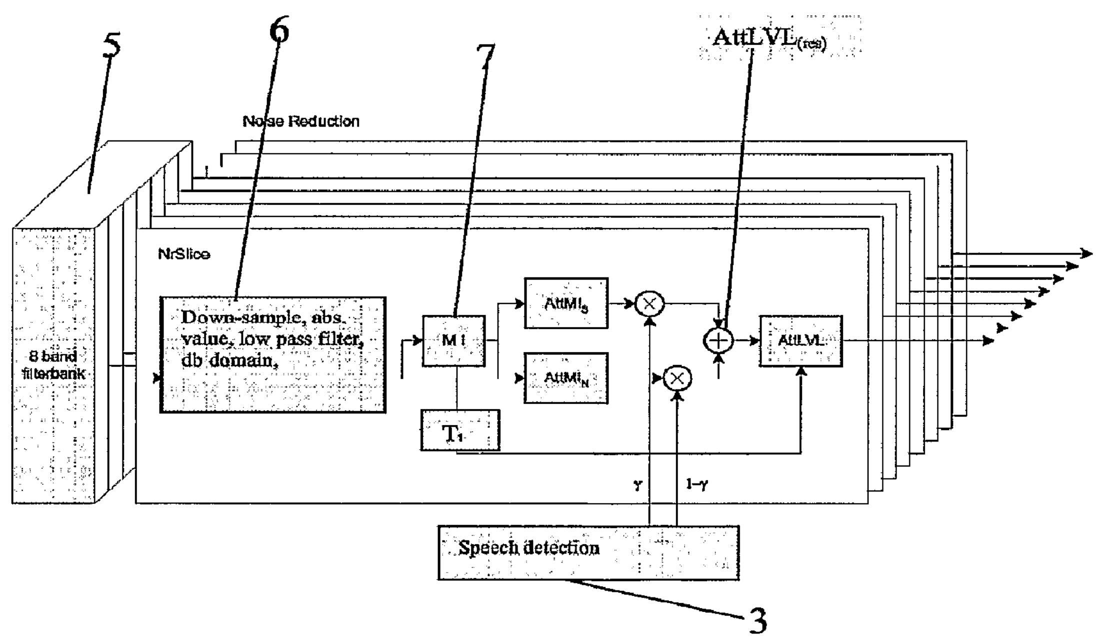
FIG. 2 shows the signal analysis in discrete frequency bands.

In FIG. 1 the overall system of the noise reduction scheme is displayed. The system is explained in relation to a hearing aid, but the noise reduction system may be used in connection with any audio system wherein noise is a problem. The audio signal is routed simultaneously to a signal analysis block 1 and to a signal processing block 2. In the signal analysis block 1 the signal is routed to a speech detector 3 and to a further detector 4 working in a number of narrow frequency bands. In FIG. 2 the filtering block 5 for the signal analysis is shown with 8 different bands according to the presented embodiment of the invention, but more or fewer bands could be employed. The signal processing block 2 will also contain some sort of narrow band operation, as band specific attenuation factors will be produced by the signal analysis block 1 as described in the following.

Figure 3:
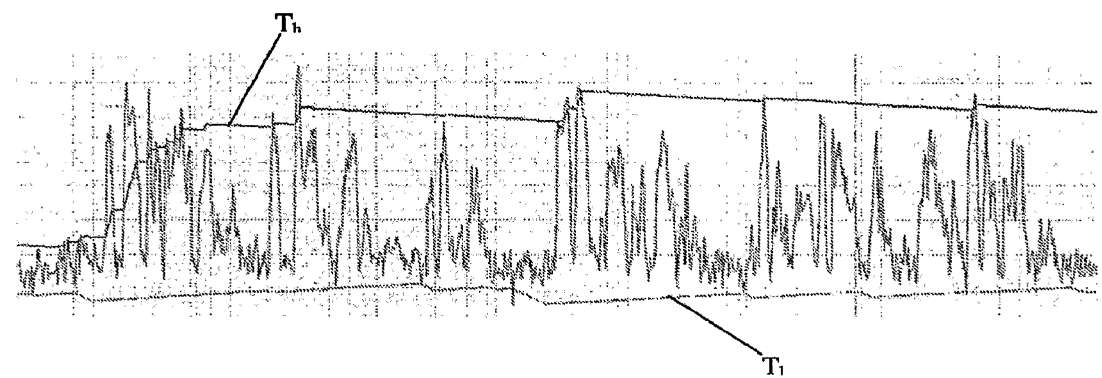
FIG. 3 is a graph showing the function of the modulation amplitude detector, FIG. 4 displays a possible dependency of the attenuation with respect to the modulation amplitude.

In the signal analysis block 1 the signal representing each of the 8 frequency bands are converted to absolute values, low-pass filtered, downsampled and converted to the Db domain in calculation block 6. The Db values are routed to a modulation amplitude detector 7. With reference to FIG. 3, it is explained how this detector works. In the graph in FIG. 3 the abscissa is a time measure and the ordinate is the Db values from the calculation block 7. The high energy parts of the signal or the peaks are tracked with short attack times and longer release times and this is shown by the upper curve $T_n$. The low energy part of the signal is tracked with moderate attack and release times and this is shown with the curve $T_1$. Thus this detector delivers band specific measures for the amplitude or size of the signal modulation in that the output is the difference between the $T_n$ and the $T_1$ values.

Figure 4:
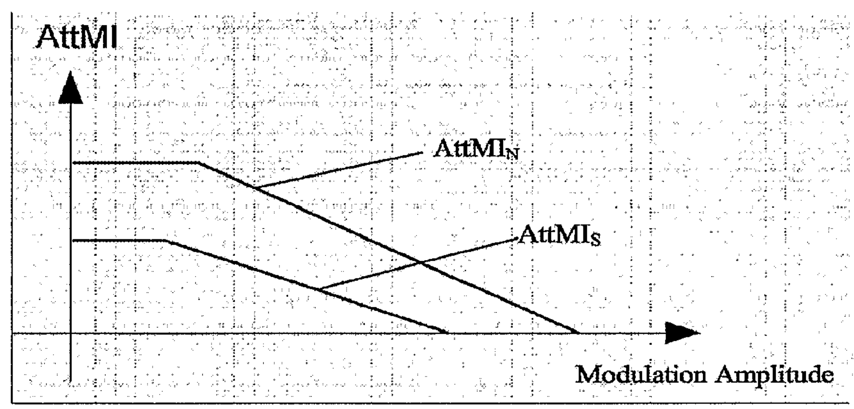

The size of the modulation is one of the determining factors for the size of the attenuation to be specified in each of the 8 frequency bands, but also the presence of speech indicators in the signal as well as the level of the signal in each band are important factors. The modulation amplitude in each frequency band is used in the following way: a first and a second transfer function $AttMI_S$ and $AttMI_N$ between the amplitude of the modulation and the wanted attenuation are specified The first transfer function named $AttMI_S$ will result in generally low attenuation values, and here the assumption is that even at slight or no modulation in the particular band, speech is present in the signal and the user only wants moderate or no damping in order not to have any parts of the speech signal dampened. The second transfer function named $AttMI_N$ will result in generally high attenuation values and here the assumption is that the signal is dominated by noise and contains no or little speech information such that the user wishes the signal to be dampened even if modulation is present in the particular band. An example of two possible transfer functions between attenuation and modulation amplitude are indicated in FIG. 4. The two transfer functions may be individually specified and may even as late as at the fitting of the hearing aid to the end-user be changed according to individual wishes. The transfer functions may be individually specified in each frequency band. The speech indicator signal which is not band specific, is used to choose which one of the transfer functions should be used, such that when the speech cues are detected the first transfer function $AtttMI_S$ is preferred and when no speech cues are detected the second transfer function $AttMI_N$ is chosen. In order to avoid abrupt shifts from low to high attenuation values a fading scheme is utilized when shifting between the two correlations:

$$AttLVL_{(res)}=\gamma(\text{speech indicator})AttMI_S+(1-\gamma(\text{speech indicator}))AttMI_N$$

Whereby the value γ is dependent on the speech indicator signal and is in the range between 0 and 1. The γ value is caused to move towards the value 1 when the speech indicator signal is positive and caused to move towards the value 0 when the speech indicator signal is negative. $AttLVL_{(res)}$ is the resulting attenuation level in the specific band.

The $AttLVL_{(res)}$ which is set in this way according to band specific modulation amplitude and according to possible speech cues in the total frequency span of the hearing aid, now need only to be regulated according to the signal level in each band.

Figure 5:
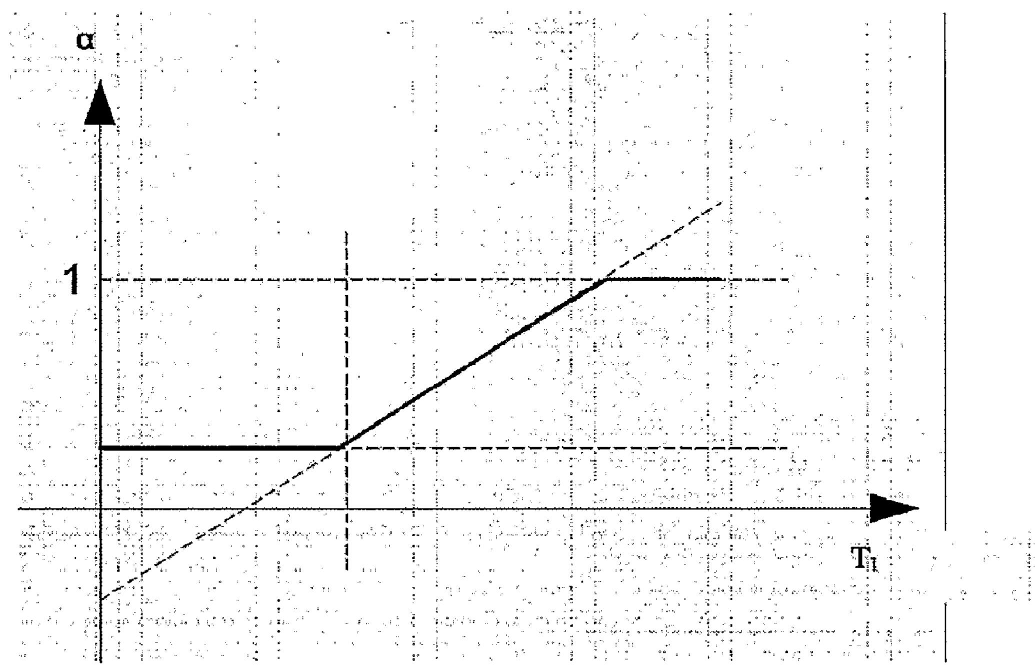
FIG. 5 is a schematic representation of a possible transfer function between noise floor and attenuation level.

With reference to FIG. 5 it is explained in the following how the $AttLVL_{(res)}$ is finally adjusted to the signal level. When the signal level is low it is preferred that low attenuation values be employed irrespective of the measure speech cues or modulation amplitudes and when the signal level is high the full impact of the calculated $AttLVL_{(res)}$ is wanted. To this end the result of the tracking function $T_1$ of the noise floor of the signal in each band is used for a final adjustment of the $AttLVL_{(res)}$ values before these are ready for output from the signal analysis part. This is done by defining a transfer function between the level of the noise floor of the signal in each frequency band $T_1$ and a scaling factor a. The $AttLVL_{(res)}$ values in each frequency band are then scaled according to this factor a. The scaling factor a is calculable through the use of the transfer function or it can be determined by use of a look up table. In FIG. 5 a possible look of the transfer function is displayed. After this scaling the final attenuation values AttLVL are ready to be used in the signal path of the hearing aid to adjust the amplification of the individual bands in order to dampen possible noise.

When the invention is implemented in a hearing aid the usual spectral amplification according to the hearing aid users need is also performed.

The invention claimed is:

1. Method for noise reduction in an audio device whereby an electrical and/or digital signal which represents sound is routed simultaneously through:

a signal analysis path, and a signal processing path wherein the signal amplification is individually controllable in specific frequency bands by attenuation values derived from the signal analysis path, whereby the signal in the signal analysis path is routed simultaneously through:

a first detector which identifies the presence of speech indicators in the overall signal, and a second detector which in a predefined number of frequency bands detects the modulation amplitude, and where attenuation values in each of the predefined frequency bands are calculated based on the combined results of the first detector and the modulation amplitude in the specific frequency band detected by the second detector, where the attenuation values in the predefined number of frequency bands are routed to the signal processing path in order to attenuate the signal level in corresponding frequency bands; and wherein the attenuation values in each specific frequency band are calculated in the following way:

first attenuation values are calculated according to a first predefined transfer function between the modulation amplitude detected by the second detector and attenuation values whereby the first transfer function prescribes generally low attenuation values, second attenuation values are calculated according to a second predefined transfer function between the modulation amplitude detected by the second detector and attenuation values whereby the second transfer function prescribes generally high attenuation values, and fading between the first and the second calculated attenuation values is performed in response to the detected speech presence indicators from the first detector.

2. Method as claimed in claim 1 whereby the second detector calculates the modulation amplitude by tracking peaks in the signal level and tracking the noise floor in the signal level and determines the distance between the overall level of the peaks and the noise floor.

3. Method as claimed in claim 2 whereby the level of the noise floor in each frequency band is used to scale the calculated corresponding attenuation value, such that higher noise floor levels results in possible higher attenuation values.

4. Method as claimed in claim 1, whereby the first detector for detecting the presence of speech indicators use statistical information relating to possible correlation of modulation in different frequency bands.

5. The method of claim 1, wherein said second detector downsamples and converts the decomposed signal in each frequency band.

6. Hearing aid with means for reducing noise in an input signal, the hearing aid including an input for receiving the input signal, and further comprising a signal analysis path, and a signal processing path having an amplification unit that amplifies the signal in frequency bands according to attenuation values derived from the signal analysis path, whereby the signal analysis path comprises:

a broad band speech detector that identifies the presence of speech indicators in the overall signal, and a band-specific analyzer that determines a modulation amplitude of the signal across a spectrum of predefined frequency bands, and where the signal analysis path further comprises an attenuation calculator that calculates attenuation values in each of the predefined frequency bands based on the combined results of the broad band speech detector and the modulation amplitudes in the predefined frequency bands as determined by the band-specific analyzer, and a signal router that routes the calculated attenuation values to the signal processing path;

where the signal processing path further comprises a signal attenuator that attenuates the signal level based on the calculated attenuation levels; and further wherein the attenuation calculator comprises:

a first attenuation calculator that calculates first attenuation values according to a first predefined transfer function between the modulation amplitude detected by the band-specific analyzer and attenuation values whereby the first transfer function prescribes generally low attenuation values, a second attenuation calculator that calculates second attenuation values according to a second predefined transfer function between the modulation amplitude detected by the band-specific analzyer and attenuation values whereby the second transfer function prescribes generally high attenuation values, a fader that fades between the first and the second calculated attenuation values in response to the detected speech presence indicators from the broad band speech detector.

7. Hearing aid as claimed in claim 6 whereby the band-specific analyzer further comprises a signal peak tracker that tracks peaks in the signal level and noise floor signal tracker that tracks the noise floor in the signal level and a peak-to-floor determination unit that determines the distance between the overall level of the peaks and the noise floor.

8. Hearing aid as claimed in claim 6 further comprising a scaling unit that scales an attenuation value in a frequency band based on a noise floor level in that frequency band, such that higher noise floor levels results in possible higher attenuation values.

9. The hearing aid of claim 6, said band-specific analyzer further comprising at least one frequency-specific downsampling and conversion unit, wherein said downsampling unit is disposed between said filter bank and said at least one frequency-specific modulation amplitude detector, and is frequency-specific to the same frequency band as its associated modulation detector.

* * * * *